(12) United States Patent
Chang et al.

(10) Patent No.: US 9,970,016 B2
(45) Date of Patent: May 15, 2018

(54) GENETIC ENGINEERED BACTERIA AND METHODS FOR PROMOTING PRODUCTION OF SUCCINIC ACID OR LACTIC ACID

(71) Applicant: Industrial Technology Research Institute, Hsinchu (TW)

(72) Inventors: Pei-Ching Chang, Hsinchu County (TW); Guang-Way Jang, Hsinchu (TW); Hsi-Yen Hsu, Hsinchu (TW); Hsiang-Yuan Chu, New Taipei (TW); Jhong-De Lin, Kaohsiung (TW); Ya-Lin Lin, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days. days.

(21) Appl. No.: 15/348,984

(22) Filed: Nov. 11, 2016

(65) Prior Publication Data
US 2017/0137829 A1    May 18, 2017

Related U.S. Application Data

(60) Provisional application No. 62/254,195, filed on Nov. 12, 2015.

(51) Int. Cl.
| | | |
|---|---|---|
| *C12N 1/20* | (2006.01) | |
| *C12N 15/63* | (2006.01) | |
| *C12N 9/04* | (2006.01) | |
| *C12N 9/10* | (2006.01) | |
| *C12N 9/12* | (2006.01) | |
| *C12P 7/46* | (2006.01) | |
| *C12P 7/56* | (2006.01) | |

(52) U.S. Cl.
CPC ........... *C12N 15/63* (2013.01); *C12N 9/0006* (2013.01); *C12N 9/1029* (2013.01); *C12N 9/1217* (2013.01); *C12P 7/46* (2013.01); *C12P 7/56* (2013.01); *C12Y 101/01001* (2013.01); *C12Y 101/01027* (2013.01); *C12Y 203/01008* (2013.01); *C12Y 207/02001* (2013.01); *C12N 2510/02* (2013.01)

(58) Field of Classification Search
CPC ..................... C12N 9/0006; C12Y 203/01008
USPC ........................................ 435/41, 136, 252.3
See application file for complete search history.

(56) References Cited

U.S. PATENT DOCUMENTS

| | | | |
|---|---|---|---|
| 7,223,567 B2 | 5/2007 | Ka-Yiu et al. | |
| 7,244,610 B2 | 7/2007 | San et al. | |
| 7,262,046 B2 | 8/2007 | Ka-Yiu et al. | |
| 7,790,416 B2 | 9/2010 | San et al. | |
| 8,647,843 B2 | 2/2014 | Yoshikawa et al. | |
| 8,962,272 B2 * | 2/2015 | San ................... | C12Y 604/0100 435/136 |
| 2006/0073577 A1 | 4/2006 | Ka-Yiu et al. | |
| 2012/0058530 A1 | 3/2012 | Zhang et al. | |

FOREIGN PATENT DOCUMENTS

| | | |
|---|---|---|
| CN | 101215582 | 7/2008 |
| CN | 102286415 A | 12/2011 |
| CN | 101608192 | 4/2012 |
| CN | 105483166 A | 4/2016 |

OTHER PUBLICATIONS

Hoefel et al. Comparative reaction engineering studies for succin acid, 2012, 7, pp. 1277-1287.*

Jusoh et al, "Characterization of Liquid Pineapple Waste as Carbon Source for Production of Succinic Acid," Jurnal Teknologi (Sciences & Engineering), Jun. 2014, pp. 11-13.

Ueno et al., "Lactic acid production using two food processing wastes, canned pineapple syrup and grape invertase, as substrate and enzyme," Biotechnology Letters, May 2003, pp. 573-577.

Chen et al, "Simultaneous saccharification and fermentation of cassava to succinic acid by *Escherichia coli* NZN111," Bioresource Technology, Apr. 18, 2014, pp. 100-105.

Zhang et al, "Metabolic evolution of energy-conserving pathways for succinate production in *Escherichia coli*," Proceedings of the National Academy of Sciences, Dec. 1, 2009, pp. 20180-20185.

Jantama et al., "Combining Metabolic Engineering and Metabolic Evolution to Develop Nonrecombinant Strains of *Escherichia coli* C That Produce Succinate and Malate," Biotechnology and Bioengineering, Oct. 30, 2007, pp. 1140-1153.

Jantama et al., "Eliminating Side Products and Increasing Succinate Yields in Engineered Strains of *Escherichia coli* C," Biotechnology and Bioengineering, Dec. 1, 2008, pp. 881-893.

Vemuri et al., "Effects of Growth Mode and Pyruvate Carboxylase on Succinic Acid Production by Metabolically Engineered Strains of *Escherichia coli*," Applied and Environmental Microbiology, Apr. 2002, pp. 1715-1727.

Sanchez et al., "Efficient Succinic Acid Production from Glucose through Overexpression of Pyruvate Carboxylase in an *Escherichia coli* Alcohol Dehydrogenase and Lactate Dehydrogenase Mutant," Biotechnol. Prog., Feb. 2005, pp. 358-365.

Andersson et al, "Effect of Different Carbon Sources on the Production of Succinic Acid Using Metabolically Engineered *Escherichia coli*," Biotechnol. Prog., Jan. 2007, pp. 381-388.

Stols et al., "Production of Succinic Acid through Overexpression of NAD1-Dependent Malic Enzyme in an *Escherichia coli* Mutant" Applied and Environmental Microbiology, Jul. 1997, pp. 2695-2701.

(Continued)

*Primary Examiner* — Tekchand Saidha
(74) *Attorney, Agent, or Firm* — Birch, Stewart, Kolasch & Birch, LLP

(57) ABSTRACT

A genetic engineered bacteria without or comprising a plurality of important metabolic enzyme related genes is provided. When the by-product or waste of fruit and vegetable is used as the culture medium, a large quantity of succinic acid or lactic acid can be produced via fermentation. A method of producing succinic acid and lactic acid using the genetic engineered bacteria is also provided.

20 Claims, No Drawings

(56) References Cited

OTHER PUBLICATIONS

Millard et al, "Enhanced Production of Succinic Acid by Overexpression of Phosphoenolpyruvate Carboxylase in *Escherichia coli*," Applied and Environmental Microbiology, May 1996, pp. 1808-1810.
Lin et al., "Genetic Reconstruction of the Aerobic Central Metabolism in *Escherichia coli* for the Absolute Aerobic Production of Succinate," Biotechnol Bioeng., Nov. 12, 2004, pp. 148-156.
Sanchez et al., "Batch culture characterization and metabolic flux analysis of succinate-producing *Escherichia coli* strains," Metabolic Engineering, Jan. 2006, pp. 209-226.
Lin et al., "Effect of Sorghum vulgare phosphoenolpyruvate carboxylase and Lactococcus lactis pyruvate arboxylase coexpression on succinate production in mutant strains of *Escherichia coli*," Appl Microbiol Biotechnol, Nov. 24, 2004, pp. 515-523.
Taiwanese Office Action and Search Report for Taiwanese Application No. 105136814, dated Apr. 11, 2017.
Hasona, A., et al, "Pyruvate Formate Lyase and Acetate Kinase Are Essential for Anaerobic Growth of *Escherichia coli* on Xylose," Journal of Bacteriology, Nov. 2004, vol. 186, No. 22, pp. 7593-7600.
Waegeman, H., et al, "Effect of icIR and arcA knockouts on biomass formation and metabolic fluxes in *Escherichia coli* K12 and its implications on understanding the metabolism of *Escherichia coli* BL21 (DE3)," BMC Microbiology, 2011, vol. 11, No. 70, pp. 1-17.

\* cited by examiner

SEQUENCE LISTING

```
<160> NUMBER OF SEQ ID NOS: 3

<210> SEQ ID NO 1
<211> LENGTH: 1284
<212> TYPE: DNA
<213> ORGANISM: Artificial Sequence
<220> FEATURE:
<223> OTHER INFORMATION: gltA

<400> SEQUENCE: 1
atggctgata caaaagcaaa actcaccctc aacgggggata cagctgttga actggatgtg      60
ctgaaaggca cgctgggtca agatgttatt gatatccgta ctctcggttc aaaaggtgtg     120
ttcacctttg acccaggctt cacttcaacc gcatcctgcg aatctaaaat tacttttatt     180
gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat ttaaaactac ggtgacccgt cataccatga tccacgagca gattacccgt     360
ctgttccatg cttccgtcg cgactcgcat ccaatggcag tcatgtgtgg tattaccggc     420
gcgctggcgg cgttctatca cgactcgctg gatgttaaca atcctcgtca ccgtgaaatt     480
gccgcgttcc gcctgctgtc gaaaatgccg accatggccg cgatgtgtta caagtattcc     540
attggtcagc catttgttta cccgcgcaac gatctctcct acgccggtaa cttcctgaat     600
atgatgttct ccacgccgtg cgaaccgtat gaagttaatc cgattctgga acgtgctatg     660
gaccgtattc tgatcctgca cgctgaccat gaacagaacg cctctacctc caccgtgcgt     720
accgctggct cttcgggtgc gaaccccgttt gcctgtatcg cagcaggtat tgcttcactg     780
tggggacctg cgcacggcgg tgctaacgaa gcggcgctga aaatgctgga agaaatcagc     840
```

| | |
|---|---:|
| tccgttaaac acattccgga atttgttcgt cgtgcgaaag acaaaaatga ttctttccgc | 900 |
| ctgatgggct tcggtcaccg cgtgtacaaa aattacgacc cgcgcgccac cgtaatgcgt | 960 |
| gaaacctgcc atgaagtgct gaaagagctg gcacgaagg atgacctgct ggaagtggct | 1020 |
| atggagctgg aaaacatcgc gctgaacgac ccgtacttta tcgagaagaa actgtacccg | 1080 |
| aacgtcgatt tctactctgg tatcatcctg aaagcgatgg gtattccgtc ttccatgttc | 1140 |
| accgtcattt tcgcaatggc acgtaccgtt ggctggatcg cccactggag cgaaatgcac | 1200 |
| agtgacggta tgaagattgc ccgtccgcgt cagctgtata caggatatga aaaacgcgac | 1260 |
| tttaaaagcg atatcaagcg ttaa | 1284 |

<210> SEQ ID NO 2
<211> LENGTH: 3623
<212> TYPE: DNA
<213> ORGANISM: Artificial Sequence
<220> FEATURE:
<223> OTHER INFORMATION: cscKAB

<400> SEQUENCE: 2

| | |
|---|---:|
| atgtcagcca aagtatgggt tttaggggat gcggtcgtag atctcttgcc agaatcagac | 60 |
| gggcgcctac tgccttgtcc tggcggcgcg ccagctaacg ttgcggtggg aatcgccaga | 120 |
| ttaggcggaa caagtgggtt tataggtcgg gtggggatg atccttttgg tgcgttaatg | 180 |
| caaagaacgc tgctaactga gggagtcgat atcacgtatc tgaagcaaga tgaatggcac | 240 |
| cggacatcca cggtgcttgt cgatctgaac gatcaagggg aacgttcatt tacgtttatg | 300 |
| gtccgcccca gtgccgatct ttttttagag acgacagact tgccctgctg cgacatggc | 360 |
| gaatggttac atctctgttc aattgcgttg tctgccgagc cttcgcgtac cagcgcattt | 420 |
| actgcgatga cggcgatccg gcatgccgga ggttttgtca gcttcgatcc taatattcgt | 480 |
| gaagatctat ggcaagacga gcatttgctc cgcttgtgtt tgcggcaggc gctacaactg | 540 |
| gcggatgtcg tcaagctctc ggaagaagaa tggcgactta tcagtggaaa acacagaac | 600 |
| gatcaggata tatgcgccct ggcaaaagag tatgagatcg ccatgctgtt ggtgactaaa | 660 |
| ggtgcagaag gggtggtggt ctgttatcga ggacaagttc accattttgc tggaatgtct | 720 |
| gtgaattgtg tcgatagcac gggggcggga gatgcgttcg ttgccgggtt actcacaggt | 780 |
| ctgtcctcta cgggattatc tacagatgag agagaaatgc gacgaattat cgatctcgct | 840 |
| caacgttgcg gagcgcttgc agtaacggcg aaaggggcaa tgacagcgct gccatgtcga | 900 |
| caagaactgg aatagaagga gatataccat gacgcaatct cgattgcatg cggcgcaaaa | 960 |
| cgccctagca aaacttcatg agcaccgggg taacactttc tatccccatt ttcacctcgc | 1020 |
| gcctcctgcc gggtggatga acgatccaaa cggcctgatc tggtttaacg atcgttatca | 1080 |
| cgcgttttat caacatcatc cgatgagcga acactggggg ccaatgcact ggggacatgc | 1140 |
| caccagcgac gatatgatcc actggcagca tgagcctatt cgctagcgc caggagacga | 1200 |
| taatgacaaa gacgggtgtt tttcaggtag tgctgtcgat gacaatggtg tcctctcact | 1260 |
| tatctacacc ggacacgtct ggctcgatgg tgcaggtaat gacgatgcaa ttcgcgaagt | 1320 |
| acaatgtctg gctaccagtc gggatggtat tcatttcgag aaacaggtg tgatcctcac | 1380 |
| tccaccagaa ggaatcatgc acttccgcga tcctaaagtg tggcgtgaag ccgacacatg | 1440 |
| gtggatggta gtcggggcga agatccagg caacacgggg cagatcctgc tttatcgcgg | 1500 |
| cagttcgttg cgtgaatgga ccttcgatcg cgtactggcc cacgctgatg cgggtgaaag | 1560 |
| ctatatgtgg gaatgtccgg actttttcag ccttggcgat cagcattatc tgatgttttc | 1620 |

-continued

```
cccgcaggga atgaatgccg agggatacag ttaccgaaat cgctttcaaa gtggcgtaat    1680
acccggaatg tggtcgccag gacgactttt tgcacaatcc gggcatttta ctgaacttga    1740
taacgggcat gacttttatg caccacaaag cttttagcg aaggatggtc ggcgtattgt    1800
tatcggctgg atggatatgt gggaatcgcc aatgccctca aaacgtgaag gatgggcagg    1860
ctgcatgacg ctggcgcgcg agctatcaga gagcaatggc aaacttctac aacgcccgt     1920
acacgaagct gagtcgttac gccagcagca tcaatctgtc tctccccgca caatcagcaa    1980
taaatatgtt ttgcaggaaa acgcgcaagc agttgagatt cagttgcagt gggcgctgaa    2040
gaacagtgat gccgaacatt acggattaca gctcggcact ggaatgcggc tgtatattga    2100
taaccaatct gagcgacttg ttttgtggcg gtattaccca cacgagaatt tagacggcta    2160
ccgtagtatt cccctcccgc agcgtgacac gctcgcccta aggatattta tcgatacatc    2220
atccgtggaa gtatttatta acgacgggga agcggtgatg agtagtcgaa tctatccgca    2280
gccagaagaa cggaactgt cgctttatgc ctcccacgga gtggctgtgc tgcaacatgg     2340
agcactctgg ctactgggtt aaaaggagat ataccatggc actgaatatt ccattcagaa    2400
atgcgtacta tcgttttgca tccagttact catttctctt tttattttcc tggtcgctgt    2460
ggtggtcgtt atacgctatt tggctgaaag gacatctagg gttgacaggg acggaattag    2520
gtacacttta ttcggtcaac cagtttacca gcattctatt tatgatgttc tacggcatcg    2580
ttcaggataa actcggtctg aagaaaccgc tcatctggtg tatgagtttc atcctggtct    2640
tgaccggacc gtttatgatt tacgtttatg aaccgttact gcaaagcaat ttttctgtag    2700
gtctaattct gggggcgcta ttttttggct tggggtatct ggcgggatgc ggtttgcttg    2760
atagcttcac cgaaaaaatg gcgcgaaatt ttcatttcga atatggaaca gcgcgcgcct    2820
ggggatcttt tggctatgct attggcgcgt tctttgccgg catatttttt agtatcagtc    2880
cccatatcaa cttctggttg gtctcgctat ttggcgctgt atttatgatg atcaacatgc    2940
gtttaaaga taaggatcac cagtgcgtag cggcagatgc gggaggggta aaaaaagagg     3000
attttatcgc agttttcaag gatcgaaact tctgggtttt cgtcatattt attgtgggga    3060
cgtggtcttt ctataacatt tttgatcaac aactttttcc tgtctttat tcaggtttat     3120
tcgaatcaca cgatgtagga acgcgcctgt atggttatct caactcattc caggtggtac    3180
tcgaagcgct gtgcatggcg attattcctt tctttgtgaa tcgggtaggg ccaaaaaatg    3240
cattacttat cggagttgtg attatggcgt tgcgtatcct ttcctgcgcg ctgttcgtta    3300
accccctggat tatttcatta gtgaagttgt tacatgccat tgaggttcca ctttgtgtca    3360
tatccgtctt caaatacagc gtggcaaact ttgataagcg cctgtcgtcg acgatctttc    3420
tgattggttt tcaaattgcc agttcgcttg ggattgtgct gctttcaacg ccgactggga    3480
tactctttga ccacgcaggc taccagacag ttttcttcgc aatttcgggt attgtctgcc    3540
tgatgttgct atttggcatt tcttcttga gtaaaaaacg cgagcaaata gttatggaaa    3600
cgcctgtacc ttcagcaata tag                                           3623
```

<210> SEQ ID NO 3
<211> LENGTH: 1623
<212> TYPE: DNA
<213> ORGANISM: Artificial Sequence
<220> FEATURE:
<223> OTHER INFORMATION: pck

<400> SEQUENCE: 3

-continued

```
atgcgcgtta caatggttt gaccccgcaa gaactcgagg cttatggtat cagtgacgta      60
catgatatcg tttacaaccc aagctacgac ctgctgtatc aggaagagct cgatccgagc     120
ctgacaggtt atgagcgcgg ggtgttaact aatctgggtg ccgttgccgt cgataccggg     180
atcttcaccg gtcgttcacc aaaagataag tatatcgtcc gtgacgatac cactcgcgat     240
actttctggt gggcagacaa aggcaaaggt aagaacgaca acaaacctct ctctccggaa     300
acctggcagc atctgaaagg cctggtgacc aggcagcttt ccggcaaacg tctgttcgtt     360
gtcgacgctt tctgtggtgc gaacccggat actcgtcttt ccgtccgttt catcaccgaa     420
gtggcctggc aggcgcattt tgtcaaaaac atgtttattc gcccgagcga tgaagaactg     480
gcaggtttca aaccagactt tatcgttatg aacggcgcga agtgcactaa cccgcagtgg     540
aaagaacagg gtctcaactc cgaaaacttc gtggcgttta acctgaccga gcgcatgcag     600
ctgattggcg gcacctggta cggcggcgaa atgaagaaag ggatgttctc gatgatgaac     660
tacctgctgc cgctgaaagg tatcgcttct atgcactgct ccgccaacgt tggtgagaaa     720
ggcgatgttg cggtgttctt cggcctttcc ggcaccggta aaaccaccct ttccaccgac     780
ccgaaacgtc gcctgattgg cgatgacgaa cacggctggg acgatgacgg cgtgtttaac     840
ttcgaaggcg gctgctacgc aaaaactatc aagctgtcga agaagcgga acctgaaatc     900
tacaacgcta tccgtcgtga tgcgttgctg gaaaacgtca ccgtgcgtga agatggcact     960
atcgactttg atgatggttc aaaaaccgag aacacccgcg tttcttatcc gatctatcac    1020
atcgataaca ttgttaagcc ggtttccaaa gcgggccacg cgactaaggt tatcttcctg    1080
actgctgatg ctttcggcgt gttgccgccg gtttctcgcc tgactgccga tcaaacccag    1140
tatcacttcc tctctggctt caccgccaaa ctggccggta ctgagcgtgg catcaccgaa    1200
ccgacgccaa ccttctccgc ttgcttcggc gcggcattcc tgtcgctgca cccgactcag    1260
tacgcagaag tgctggtgaa acgtatgcag gcggcgggcg cgcaggctta tctggttaac    1320
actggctgga acggcactgg caaacgtatc tcgattaaag ataccgcgc cattatcgac    1380
gccatcctca acggttcgct ggataatgca gaaaccttca ctctgccgat gtttaacctg    1440
gcgatcccaa ccgaactgcc gggcgtagac acgaagattc tcgatccgcg taacacctac    1500
gcttctccgg aacagtggca ggaaaaagcc gaaaccctgg cgaaactgtt tatcgacaac    1560
ttcgataaat acaccgacac ccctgcgggt gccgcgctgg tagcggctgg tccgaaactg    1620
taa                                                                   1623
```

GENETIC ENGINEERED BACTERIA AND METHODS FOR PROMOTING PRODUCTION OF SUCCINIC ACID OR LACTIC ACID

CROSS-REFERENCE TO RELATED APPLICATION

This application claims the priority benefits of U.S. provisional application Ser. No. 62/254,195, filed on Nov. 12, 2015. The entirety of the above-mentioned patent application is hereby incorporated by reference herein and made a part of this specification.

TECHNICAL FIELD

The disclosure relates to a genetic engineered bacteria utilized for promoting succinic acid or lactic acid production and a method used thereof.

BACKGROUND

The current biochemicals still mostly adopt food materials such as corn starch or glucose as the carbon source, but in the long run, it may cause scarcity in food and land in the future, thus resulting in competition in energy and food production.

The data of the Council of Agriculture shows that, over 5 million tons of agricultural waste is produced in Taiwan each year, in which agricultural waste is greater than 2 million tons. In terms of vegetable waste, the water content thereof reaches 90% or more, and burying not only occupies space, but also causes problems of leakage to the landfill, thereby resulting in secondary pollution. However, the processing costs of incineration treatment may be increased due to high water content and insufficient calorific value.

Therefore, the effective recycling and reuse of agricultural waste and turning the agricultural waste into energy (such as livestock manure biogas fermentation) or resource (such as carbonization of rice husk, fish scale collagen, and extraction of chitin from oyster shell) based on the characteristics of the waste to create economic benefits have become important means for agricultural management and energy development.

In response to the rapid growth of green products in the market demand, the production and development of biogenic succinic acid and lactic acid are important. The application scope of succinic acid and lactic acid is relatively wide, and succinic acid can be used as an intermediate product for the production of coating, ink, and dye, and can also be applied in, for instance, the metal processing industry, pharmaceutical industry, food, and polymer industry. In addition to industries such as leather and textile manufacturing, lactic acid also plays an important role in the application of fields such as medicine, food, and wine making.

Therefore, the development of a method that both allows recycling of agricultural waste and promotes production of succinic acid or lactic acid has become an important topic in the industry.

SUMMARY

The disclosure provides a genetic engineered bacteria producing succinic acid using a fruit and vegetable by-product or fruit and vegetable waste as a metabolic substrate, the genetic engineered bacteria comprising: a knock out endogenous ldhA gene that does not express lactate dehydrogenase (LDH); a knock out endogenous adhE gene that does not express alcohol dehydrogenase (ADH); and a knock out endogenous ackA-pta gene that does not express acetate kinase and phosphotransacetylase (ACK-PTA); in which the genetic engineered bacteria is cultured in a culture medium, and the culture medium comprises at least one fruit and vegetable by-product or fruit and vegetable waste as a carbon source of the genetic engineered bacteria to produce succinic acid.

The disclosure also provides a method for producing succinic acid with the genetic engineered bacteria, comprising the following steps: first, the genetic engineered bacteria is provided; next, a culture medium is provided, in which the culture medium comprises at least one fruit and vegetable by-product or a fruit and vegetable waste as a carbon source of the genetic engineered bacteria; then, the genetic engineered bacteria is cultured in the culture medium at a culture temperature of 26° C. to 40° C. and a pH value ranging from 6 to 8 to produce a culture solution, such that the genetic engineered bacteria produces succinic acid into the culture solution with the fruit and vegetable by-product or fruit and vegetable waste as the metabolic substrate thereof; thereafter, the culture solution comprising succinic acid is collected. Next, succinic acid is isolated from the culture solution comprising succinic acid.

The disclosure further provides a genetic engineered bacteria producing lactic acid using a fruit and vegetable by-product or a fruit and vegetable waste as a metabolic substrate, comprising: a knock out endogenous adhE gene that does not express alcohol dehydrogenase (ADH); and a knock out endogenous ackA-pta gene that does not express acetate kinase and phosphotransacetylase (ACK-PTA); in which the genetic engineered bacteria is cultured in a culture medium, and the culture medium comprises at least one fruit and vegetable by-product or fruit and vegetable waste as a carbon source of the genetic engineered bacteria to produce lactic acid.

The disclosure further provides a method for producing lactic acid with the genetic engineered bacteria, comprising the following steps: first, the genetic engineered bacteria is provided; next, a culture medium is provided, in which the culture medium comprises at least one fruit and vegetable by-product or fruit and vegetable waste as a carbon source of the genetic engineered bacteria; then, the genetic engineered bacteria is cultured in the culture medium at a culture temperature of 26° C. to 40° C. and a pH value ranging from 6 to 8 to produce a culture solution, such that the genetic engineered bacteria produces lactic acid into the culture solution with the fruit and vegetable by-product or fruit and vegetable waste as the metabolic substrate thereof; thereafter, the culture solution comprising lactic acid is collected. Next, lactic acid is isolated from the culture solution comprising lactic acid.

Several exemplary embodiments accompanied with tables are described in detail below to further describe the disclosure in details.

DETAILED DESCRIPTION OF DISCLOSED EMBODIMENTS

Embodiments

In the present disclosure, "knock out endogenous gene" refers to, or instance, point mutation, deletion, or insertion of the endogenous gene such that the endogenous gene cannot produce functional peptide. In particular, after knocking out the endogenous gene of the mutant bacteria, complete knock out of the endogenous gene is confirmed via polymerase chain reaction (PCR), and therefore the mutant bacteria cannot produce functional peptide. For instance, the endogenous ldhA gene encodes lactate dehydrogenase, but the knock out endogenous ldhA gene does not express lactate dehydrogenase.

In one embodiment of the disclosure, a genetic engineered bacteria producing succinic acid using a fruit and vegetable by-product or fruit and vegetable waste as a metabolic substrate is provided, the genetic engineered bacteria comprising: a knock out endogenous ldhA gene that does not express lactate dehydrogenase (LDH); a knock out endogenous adhE gene that does not express alcohol dehydrogenase (ADH); and a knock out endogenous ackA-pta gene that does not express acetate kinase and phosphotransacetylase (ACK-PTA); in which the genetic engineered bacteria is cultured in a culture medium, and the culture medium comprises at least one fruit and vegetable by-product or fruit and vegetable waste as a carbon source of the genetic engineered bacteria to produce succinic acid.

The fruit and vegetable by-product or waste refers to non-economic products in the fruit and vegetable production process, and includes overproduced fruit and vegetable, fruit and vegetable waste containing peel, root, and leaf after removal of edible or usable pulp, or fruit and vegetable waste after product processing. The type of the fruit and vegetable can be, for instance, a temperate fruit, a subtropical fruit, a tropical fruit, or a root vegetable. In particular, the temperate fruit is, for instance, apple or pear, the subtropical fruit is, for instance, lemon, orange, grapefruit, or watermelon, the tropical fruit is, for instance, pineapple, mango, or banana, and the root vegetable is, for instance, carrot or onion. The types of the fruits and vegetables are only exemplary and the disclosure is not limited thereto.

The at least one fruit and vegetable by-product or fruit and vegetable waste in the culture medium refers to selecting at least one or any two or more by-products or waste from the above-mentioned fruits and vegetables, and then mixing and adding to the culture medium as the carbon source for the genetic engineered bacteria.

The fruit and vegetable by-product or fruit and vegetable waste is measured after collection, in which the carbon source including 5 g/L to 210 g/L of glucose, 0.5 g/L to 50 g/L of sucrose, and 1 g/L to 55 g/L of fructose are provided, as well as protein concentration of about 0.03 mg/mL to 0.8 mg/mL, pH value ranging from about 2.5 to 6, and nitrogen source ranging from about 470 mg/L to 1740 mg/L are measured.

Moreover, after pretreatments such as high temperature sterilization are performed on the collected fruit and vegetable by-product or fruit and vegetable waste, the fruit and vegetable by-product or fruit and vegetable waste is adjusted to contain a carbon source of 5 g/L to 50 g/L of glucose, 0.5 g/L to 50 g/L of sucrose, and 2 g/L to 60 g/L of fructose. Thereafter, the fruit and vegetable by-product or fruit and vegetable waste with above-mentioned ingredients and concentration is mixed with a solution to form a culture medium. During the bacteria culture, the culture temperature of the culture medium is adjusted to 26° C. to 40° C., and the pH value thereof is adjusted to 6 to 8.

In another embodiment of the disclosure, about 1 g/L to 50 g/L of sodium bicarbonate can be further added to the culture medium. Moreover, the genetic engineered bacteria can be cultured in an anaerobic or aerobic state. In particular, aerobic refers to 0.1% to 10% of dissolved oxygen. In particular, the culture time of anaerobic culture is about 12 hours to 120 hours, and the culture time of aerobic culture is about 12 hours to 48 hours.

In another embodiment of the disclosure, a method for producing succinic acid with the genetic engineered bacteria is also provided, comprising the following steps: first, the genetic engineered bacteria is provided; next, a culture medium is provided, in which the culture medium contains at least one fruit and vegetable by-product or fruit and vegetable waste as a carbon source of the bacteria; then, the genetic engineered bacteria is cultured in the culture medium at a culture temperature of 26° C. to 40° C. and a pH value ranging from 6 to 8 such that the genetic engineered bacteria produces succinic acid into the culture solution with the fruit and vegetable by-product or fruit and vegetable waste as the metabolic substrate thereof; thereafter, the culture solution comprising succinic acid is collected. Next, succinic acid is isolated from the culture solution comprising succinic acid.

In yet another embodiment of the disclosure, a genetic engineered bacteria producing lactic acid using a fruit and vegetable by-product or fruit and vegetable waste as a metabolic substrate is provided, comprising: a knock out endogenous adhE gene that does not express alcohol dehydrogenase (ADH); and a knock out endogenous ackA-pta gene that does not express acetate kinase and phosphotransacetylase (ACK-PTA); in which the genetic engineered bacteria is cultured in a culture medium, and the culture medium comprises at least one fruit and vegetable by-product or fruit and vegetable waste as a carbon source of the bacteria to produce lactic acid.

In particular, the definition of the fruit and vegetable by-product or fruit and vegetable waste, the type of the fruits and vegetables, the measured carbon source range, protein concentration, pH value, nitrogen source range of the collected fruit and vegetable by-product or fruit and vegetable waste, and the provided carbon source range, culture temperature, pH value, amount of sodium bicarbonate added, and culture time after processing and adjusting of the culture stage are all described in the above paragraphs and are not repeated herein.

In yet another embodiment of the disclosure, a method for producing lactic acid with the genetic engineered bacteria is provided, comprising the following steps: first, the genetic engineered bacteria is provided; next, a culture medium is provided, in which the culture medium comprises at least one fruit and vegetable by-product or fruit and vegetable waste as a carbon source of the genetic engineered bacteria; then, the genetic engineered bacteria is cultured in the culture medium at a culture temperature of 26° C. to 40° C. and a pH value ranging from 6 to 8 such that the genetic engineered bacteria produces lactic acid into the culture solution with the fruit and vegetable by-product or fruit and vegetable waste as the metabolic substrate thereof; thereafter, the culture solution comprising lactic acid is collected. Next, lactic acid is isolated from the culture solution comprising lactic acid.

In the following, specific embodiments are provided to specifically describe the implementation method:

The bacteria and plasmids used in the embodiments of the disclosure and the relevant genotypes of the bacteria and plasmids are shown in Table 1. In particular, strain BW25113 is used as the wild type (WT), and the corresponding genotype thereof is: rrnBT14 ΔlacZWJ16 hsdR514 ΔaraBADAH33 ΔrhaBADLD78 (refer to DAtsenko and Wanner, 2000 *One-step inactivation of chromosomal genes in Escherichia coli K-12 using PCR products. Proc. Natl. Acad. Sci. U.S.A.* 97(12):6640-5).

TABLE 1

Bacteria and plasmids used in the embodiments of the disclosure

| Name | Relevant genotype |
|---|---|
| Bacteria (Strains) | |
| BW25113 | (rrnBT14 ΔlacZWJ16 hsdR514 ΔaraBADAH33 ΔrhaBADLD78) |
| PCI 634 | BW25113 but ΔackA-pta Δ adhE Δ ldhA |
| PCI 634AS196 | 634/pCS58/pCS196 |
| PCI 627 | BW25113 but ΔackA-pta Δ adhE |
| JD640 | BW25113 but ΔackA-pta ΔadhE ΔldhA ΔptsG |
| JD645 | JD640/JDP01 |
| JD652 | JD640/JDP02MS |
| JD654 | JD640/JDP01/JDP02MS |
| Plasmid | |
| pCS58 | ColE1 on; SpeR; PLlacO1::gltA (SEQ: 1) |
| pCS196 | from pSA40 pSC101 on; AmpR; pLacO1:: CSCKAB (SEQ: 2) |
| JDP01 | from pSA40 ColE1 on; KanR; pLacO1:: pck (SEQ: 3) |
| JDP02MS | from pSA40 ColE1 on; AmpR; pLacO1:: CSCKAB |

Fermentation Production of Succinic Acid

Experiment 1: Production of Succinic Acid with Pineapple Juice Produced by Different Processing Methods as Culture Medium 1. Origin and Pretreatment of Pineapple Juice Pineapple juice (PAJ) produced from pineapple waste refers to PAJ obtained by processing overproduced pineapple waste containing peel, root, and leaf after removal of the usable pulp. In particular, the processing method of pineapple waste includes: (A) pineapple waste containing skin, root, and leaf was smashed and centrifuged, then the pomace was removed to obtain pineapple juice; (B) pineapple waste containing skin, root, and leaf was smashed and filtered, then the pomace was removed to obtain pineapple juice; (C) pineapple waste containing skin, root, and leaf was pressed to obtain pineapple juice without pomace. The pH value of the pineapple juice obtained by above-mentioned three methods was between about 3.3 and 4.0, the measured glucose was about 20 g/L to 40 g/L, the measured sucrose was about 4 g/L to 34 g/L, and the measured fructose was about 28 g/L to 53 g/L. Moreover, the total nitrogen content and the protein concentration were analyzed to be about 470 mg/L to 880 mg/L and 0.03 mg/mL to 0.66 mg/mL, respectively, and the pineapple juice could be directly used as the substrate of the culture medium after high-temperature sterilization.

2. Production of Succinic Acid Using Genetic Engineered Bacteria with Above-Mentioned (A) PAJ as the Culture Medium First, the PAJ culture medium obtained by method (A) (hereinafter (A) PAJ culture medium) was provided, in which the PAJ culture medium comprises a carbon source (including 20 g/L to 40 g/L of glucose, 4 g/L to 34 g/L of sucrose, and 28 g/L to 53 g/L of fructose), a phosphate buffer solution, and 0.5 mM isopropylthiog-galactoside (IPTG). Next, the bacteria strain PCI 634 was cultured in LB culture medium (luria broth, a nutrient medium commonly used in microbial culture) overnight at 37° C. prior to inoculating in a bioreactor containing the above-mentioned (A) PAJ culture medium. Moreover, a phosphate buffer (PB) containing 0.15 g/L to 5 g/L ammonium chloride, 2.5 g/L yeast extract, and 5 g/L yeast extract were respectively used as control groups, in which the carbon source (glucose, sucrose, and fructose) was respectively added to each control group with an equivalent amount to the carbon source of the experimental group (A) PAJ. Thereafter, the control groups were aerobically cultured in a shake flask at 37° C. and pH 7 for 48 hours. Then, the concentration of succinic acid was analyzed and the results are shown in Table 2.

TABLE 2

Production of succinic acid by bacteria strain PCI 634 expressed in groups of different culture media but equivalent carbon source

| Culture medium | Produced succinic acid (g/L) |
|---|---|
| (A) PAJ | 2.88 ± 0.64 |
| PB | 0.79 |
| 2.5 g/L yeast extract | 0.69 |
| 5 g/L yeast extract | 0.66 |

3. Production of Succinic Acid Using Genetic Engineered Bacteria with Above-Mentioned (B) PAJ as Culture Medium First, a PAJ culture medium obtained by method (B) (hereinafter (B) PAJ culture medium) was provided. Next, the bacteria strain PCI 634 was cultured in LB culture medium overnight at 37° C. prior to inoculating in a bioreactor containing the above-mentioned (B) PAJ culture medium. Moreover, PB containing 0.15 g/L to 5 g/L ammonium chloride, 2.5 g/L yeast extract, and 5 g/L yeast extract were respectively used as control groups, in which the carbon source (glucose, sucrose, and fructose) was respectively added to each control group with an equivalent amount to the carbon source of the experimental group (B) PAJ. Thereafter, the control groups were aerobically cultured in a shake flask at 37° C. and pH 7 for 48 hours. Then, the concentration of succinic acid was analyzed and the results are shown in Table 3.

TABLE 3

Production of succinic acid by bacteria strain PCI 634 expressed in groups of different culture media but equivalent carbon source

| Group | Produced succinic acid (g/L) |
|---|---|
| (B) PAJ | 3.90 ± 1.34 |
| PB | 0.68 |
| 2.5 g/L yeast extract | 0.72 |
| 5 g/L yeast extract | 0.67 |

4. Production of Succinic Acid Using Genetic Engineered Bacteria with Above-Mentioned (C) PAJ as Culture Medium First, a PAJ culture medium obtained by method (C) (hereinafter (C) PAJ culture medium) was provided. Next, the bacteria strain PCI 634 was cultured in LB culture medium overnight at 37° C. prior to inoculating in a bioreactor containing the above-mentioned (C) PAJ culture medium. Moreover, PB containing 0.15 g/L to 5 g/L ammonium chloride, 2.5 g/L yeast extract, and 5 g/L yeast extract were respectively used as control groups, in which the carbon source (glucose, sucrose, and fructose) was respectively added to each control group with an equivalent amount to the carbon source of the experimental group (C) PAJ. Thereafter, the control groups were aerobically cultured in a shake flask at 37° C. and pH 7 for 48 hours. Then, the concentration of succinic acid was analyzed and the results are shown in Table 4.

TABLE 4

Production of succinic acid by bacteria strain PCI 634 expressed in groups of different culture media but equivalent carbon source

| Group | Produced succinic acid (g/L) |
|---|---|
| (C) PAJ | 3.02 ± 0.45 |
| PB | 0.70 |
| 2.5 g/L yeast extract | 0.69 |
| 5 g/L yeast extract | 0.68 |

Experiment 2: Production of Succinic Acid Under Different Culture Conditions

1. Bacteria

The bacteria strain PCI 634AS196 was used, and a plasmid cscKAB that can express a large number of sucrose metabolism related genes (such as genes cscK, cscA and cscB, which are collectively called gene cscKAB (such as SEQ:2) herein) was incorporated into the bacteria 634 to promote sucrose decomposition in the juice into monosaccharide and strengthen the expression of citric acid metabolism gene gltA (such as SEQ:1) to effectively convert the monosaccharide into succinic acid.

2. Testing of Succinic Acid Production at Different Culture pH Values

The bacteria strain PCI 634AS196 was first cultured in LB culture medium overnight at 37° C., and then was inoculated in a bioreactor containing the above-mentioned (A) PAJ culture medium. Aerobic culture was first performed for 7 hours under the culture conditions of a temperature of 30° C. and a pH value at 6.4, 6.8, 7.2, and 7.6 respectively, and then 8 g/L of sodium bicarbonate was added. Thereafter, after anaerobic culture for 41 hours, the concentration of succinic acid was analyzed, and the results are shown in Table 5.

TABLE 5

Production of succinic acid by bacteria strain PCI 634AS196 expressed at different pH values

| pH value | Succinic acid (g/L) |
|---|---|
| 6.4 | 5.56 |
| 6.8 | 7.22 |
| 7.2 | 8.11 |
| 7.6 | 6.75 |

3. Testing of Succinic Acid Production at Different Culture Temperatures

The bacteria strain PCI 634AS196 was first cultured in LB culture medium overnight at 37° C., and then was inoculated in a bioreactor containing the above-mentioned (A) PAJ culture medium. Aerobic culture was first performed to an OD value between 2.5 and 3 under the culture conditions of a pH value of 7.2 and a temperature at 28° C., 34° C., 37° C., and 39° C. respectively, and then 6 g/L of sodium bicarbonate was added. Thereafter, after anaerobic culture for 40 to 43 hours, the concentration of succinic acid was analyzed, and the results are shown in Table 6.

TABLE 6

Production of succinic acid by bacteria strain PCI 634AS196 expressed at different temperatures

| Temperature (° C.) | Succinic acid (g/L) |
|---|---|
| 28 | 7.18 |
| 34 | 10.07 |
| 37 | 8.99 |
| 39 | 7.41 |

4. Production of Succinic Acid Under Changes in Aerobic and Anaerobic Culture Time The bacteria strain PCI 634 was first cultured in LB culture medium overnight at 37° C., and then was inoculated in a bioreactor containing the above-mentioned (A) PAJ culture medium. Aerobic culture was first performed for 24 hours under the culture conditions of 34° C. and a pH of 7.2, then 10 g/L of sodium bicarbonate was added, and then after anaerobic culture for 24 hours, the content of succinic acid was analyzed. Moreover, 5 g/L of yeast extract was used as the control group, in which the carbon source (glucose, sucrose, and fructose) was added with an equivalent amount to the carbon source of the experimental group (A) PAJ, and the measurement results are shown in Table 7.

TABLE 7

Production of succinic acid by bacteria strain PCI 634 expressed under changes in aerobic and anaerobic culture time

| Group | Succinic acid (g/L) |
|---|---|
| (A) PAJ | 3.28 |
| Yeast extract | 1.34 |

Experiment 3: Succinic Acid Production of Other Modified Bacteria

1. Bacteria

The bacteria strain JD645 was used, and in comparison to the bacteria strain 634, the bacteria strain JD645 had an additional knock out gene ptsG and the expression of gene pck (such as SEQ:3) was increased to strengthen the metabolic pathway of phosphoenolpyruvate (PEP) toward oxalacetate (OAA) and reduce the consumption of glucose.

2: Testing of Succinic Acid Production in Other Modified Bacteria Strains

The bacteria strain JD645 was first cultured in LB culture medium overnight at 37° C., and then was inoculated in a bioreactor containing the above-mentioned (B) PAJ and (C) PAJ culture media. Aerobic culture was first performed for 24 hours under the culture conditions of 34° C. and pH 7.2, and then 20 g/L of sodium bicarbonate was added. Thereafter, after anaerobic culture for 120 hours, the content of succinic acid was analyzed, and the results are shown in Table 8.

TABLE 8

Production of succinic acid by bacteria strain JD645
expressed in various PAJ culture media produced via
different processing methods

| Group | Succinic acid (g/L) |
|---|---|
| (B) PAJ | 17.39 |
| (C) PAJ | 12.15 |

Experiment 4: Production of Succinic Acid with
Concentrated Orange Juice as Culture Medium 1. Origin and Pretreatment of Concentrated Orange Juice The orange juice was mainly from expired or leftover products of juice factories, in which the orange juice was not provided to consumers and made into orange juice concentrate (OJC) without pomace, and the pH value thereof was about 3 to 4, the measured glucose content was about 100 g/L to 210 g/L, and the protein concentration was about 0.03 mg/mL to 0.1 mg/mL. Otherwise, filtering procedure was not needed in the pretreatment process of the OJC, but high-temperature sterilization was still needed to be performed before the orange juice concentrate directly used as the culture medium.

2. Production of Succinic Acid Using Genetic Engineered Bacteria with OJC as Culture Medium An OJC-based culture medium was provided, which contains OJC (20 g/L to 25 g/L of glucose), PB solution, and 0.5 mM of IPTG. The bacteria strain JD652 is based on strain JD640 and incorporates the plasmid cscKAB that can express large numbers of sucrose metabolism related genes to increase sucrose decomposition in the juice into monosaccharide. Moreover, the bacteria strain JD645 was used as the control group.

The bacteria strains JD652 and JD640 were first cultured in LB culture medium overnight at 37° C., and then were inoculated in a bioreactor containing the 10% OJC culture medium (20 g/L to 25 g/L of glucose). Moreover, PB containing 0.15 g/L to 5 g/L of ammonium chloride was used as the control group, in which the carbon source was added with an equivalent amount to the carbon source of the experimental group 10% OJC. Aerobic culture was first performed for 24 hours under the culture conditions of 34° C. and pH 7.2, and then 10 g/L of sodium bicarbonate was added. Thereafter, after anaerobic culture for 96 hours, the content of succinic acid was analyzed, and the results are shown in Table 9.

TABLE 9

Production of succinic acid by bacteria strains JD652 and
JD640 expressed in 10% OJC culture medium

| Bacteria | Culture medium | Succinic acid (g/L) |
|---|---|---|
| JD645 | 10% OJC | 6.33 |
|  | PB | 5.37 |
| JD652 | 10% OJC | 9.07 |
|  | PB | 8.75 |

Experiment 5: Production of Succinic Acid with
Discarded Carrot Fruit Juice as Culture Medium 1. Origin and Pretreatment of Carrot Fruit Juice Since sampled products cannot be provided to consumers, QC (quality control) sampling products from juice factory production lines were mainly used, which are hereinafter referred to as discarded carrot fruit juice (CFJ). In particular, carrot was used as the main component, and at least one or more of other juices were added, and the discarded CFJ did not contain pomace. Moreover, the pH value of CFJ was about 4 to 5, the measured carbon source content was about: 5 g/L to 10 g/L of glucose, 35 g/L to 50 g/L of sucrose, and 15 g/L to 30 g/L of fructose, and the total nitrogen content and protein concentration were analyzed to be about 470 mg/L to 500 mg/L and about 0.03 mg/mL to 0.1 mg/mL, respectively. Otherwise, filtering procedure was not required in the pretreatment process of the CFJ, but high-temperature sterilization was required to be performed before the CFJ directly used as the culture medium.

2. Production of Succinic Acid Using Genetic Engineered Bacteria with CFJ as Culture Medium A CFJ-based culture medium was provided, which contains CFJ (9 g/L of glucose, 45 g/L of sucrose, and 25 g/L of fructose), PB solution, and 0.5 mM of IPTG. Bacteria strain JD654 was used, which is based on JD640 and incorporates plasmids pck and cscKAB to strengthen metabolic pathway and promote sucrose decomposition in the juice into monosaccharide.

The bacteria strain JD654 was first cultured in LB culture medium overnight at 37° C., and then was inoculated in a bioreactor containing the CFJ culture medium. Moreover, PB containing 0.15 g/L to 5 g/L of ammonium chloride was used as the control group, in which the carbon source was added with an equivalent amount to the carbon source of the experimental group CFJ. Thereafter, 10 g/L of sodium bicarbonate was added under the culture conditions of 34° C. and pH 7.2. Then, after anaerobic culture for 72 hours, the content of succinic acid was analyzed, and the results are shown in Table 10.

TABLE 10

Production of succinic acid by bacteria strain JD654
expressed in CFJ culture medium

| Culture medium | Succinic acid (g/L) |
|---|---|
| CFJ | 3.81 |
| PB | 1.17 |

3. Production of Succinic Acid Using Genetic Engineered Bacteria with CFJ and OJC as Culture Medium A CFJ-based culture medium was provided, which contains CFJ+10% OJC (containing 30 g/L to 35 g/L of glucose, 35 g/L to 40 g/L of sucrose, and 40 g/L to g/L of fructose), PB solution, and 0.5 mM of IPTG. The bacteria strain JD654 was used, which is based on JD645 and incorporates plasmid cscKAB that can express large numbers of sucrose metabolism related genes to increase sucrose decomposition in the juice into monosaccharide and promote the production of succinic acid. At the same time, the bacteria strain JD645 was also used as the control group.

The bacteria strains JD645 and JD654 were first cultured in LB culture medium overnight at 37° C., and then were inoculated in a bioreactor containing the CFJ+10% OJC culture medium. Aerobic culture was first performed for 24 hours under the culture conditions of 34° C. and pH 7.2, and then 10 g/L of sodium bicarbonate was added. Thereafter, after anaerobic culture for 96 hours, the content of succinic acid was analyzed, and the results are shown in Table 11.

TABLE 11

Production of succinic acid by bacteria strains JD645 and
JD654 expressed in CFJ + 10% OJC culture medium

| Bacteria | Succinic acid (g/L) |
| --- | --- |
| JD645 | 9.12 |
| JD654 | 10.63 |

Experiment 6: Production of Succinic Acid with
Non-Seasonal Orange Juice as Culture Medium 1. Origin and Pretreatment of Orange Juice Commercially-available non-seasonal orange juice (OJ) containing pulp stored in freezing environment was mainly used, in which the pH value thereof was about 2.5 to 4, the measured carbon source content was about: 15 g/L to 35 g/L of glucose, 25 g/L to 55 g/L of sucrose, and 25 g/L to 55 g/L of fructose, and the protein concentration was about 0.03 mg/mL to 0.1 mg/mL. Otherwise, filtering procedure was not required in the pretreatment process of the OJ, but high-temperature sterilization was required to be performed before the OJ directly used as the culture medium.

2. Production of Succinic Acid Using Genetic Engineered Bacteria with OJ as Culture Medium An OJ-based culture medium was provided, which contains 50% OJ (containing 10 g/L to 15 g/L of glucose, 16 g/L to 20 g/L of sucrose, and 20 g/L to 25 g/L of fructose), PB solution, and 0.5 mM of IPTG. The bacteria strain JD654 was first cultured in LB culture medium overnight at 37° C., and then was inoculated in a bioreactor containing the 50% OJ culture medium. Moreover, PB containing 0.15 g/L to 5 g/L of ammonium chloride was used as the control group, in which the carbon source was added with an equivalent amount to the carbon source of the experimental group 50% OJ. Thereafter, 10 g/L of sodium bicarbonate was added under the culture conditions of 34° C. and pH 7.2, and then after anaerobic culture for 72 hours, the content of succinic acid was analyzed, and the results are shown in Table 12.

TABLE 12

Production of succinic acid by bacteria strain JD654
expressed in 50% OJ culture medium

| Culture medium | Succinic acid (g/L) |
| --- | --- |
| OJ | 3.34 |
| PB | 1.17 |

Experiment 7: Production of Succinic Acid with
Agricultural Waste Lemon Peel Juice as Culture
Medium 1. Origin and Pretreatment of Lemon Peel Juice Agricultural waste lemon peel juice (LPJ) refers to lemon peel waste remaining after usable pulp is removed. The processing method of LPJ was: after lemon peel was shredded, the lemon peel was pulverized via a high-speed pulverizer, and water extraction was performed using a lemon peel:RO (reverse osmosis) water ratio of 3:2 for 30 minutes, and then centrifugation was performed using an ultra-high-speed centrifuge at 6000 g for 20 minutes. Thereafter, the supernatant was retained, and the supernatant was sieved using a coarse sieve and a fine sieve, and then suction filtration was performed using non-woven fabric as the membrane filter to obtain an LPJ (suspended finely divided solid particles of lemon peel) without large particles of lemon peel. The pH value of LPJ was about 3 to 3.65, the measured carbon source content was about: 5 g/L to 10 g/L of glucose, 1 g/L to 10 g/L of sucrose, and 2 g/L to 10 g/L of fructose, the total nitrogen content was about 1500 mg/L to 1740 mg/L, and the protein concentration was about 0.1 mg/mL to 0.2 mg/mL, and LPJ could be directly used as the culture medium after high-temperature sterilization.

2. Production of Succinic Acid Using Genetic Engineered Bacteria with LPJ and OJC as Culture Medium An LPJ-based culture medium was provided, which contains LPJ+10% OJC (containing 25 g/L to 35 g/L of glucose, 0.5 g/L to 2 g/L of sucrose, and 25 g/L to 30 g/L of fructose), PB solution, and 0.5 mM of IPTG. The bacteria strains JD645 and JD654 were first cultured in LB culture medium overnight at 37° C., and then were inoculated in a bioreactor containing the LPJ+10% OJC culture medium. Aerobic culture was first performed for 24 hours under the culture conditions of 34° C. and pH 7.2, then 10 g/L of sodium bicarbonate was added. Thereafter, after anaerobic culture for 96 hours, the content of succinic acid was analyzed, and the results are shown in Table 13.

TABLE 13

Production of succinic acid by bacteria strains JD645 and
JD654 expressed in LPJ + 10% OJC culture medium

| Bacteria | Succinic acid (g/L) |
| --- | --- |
| JD645 | 2.12 |
| JD654 | 3.58 |

3. Production of Succinic Acid Using Genetic Engineered Bacteria with LPJ and OJ as Culture Medium The culture medium contains LPJ+50% OJ (containing 20 g/L to 25 g/L of glucose, 5 g/L to 10 g/L of sucrose, and 25 g/L to 30 g/L of fructose), PB solution, and 0.5 mM of IPTG. The bacteria strain JD654 was first cultured in LB culture medium overnight at 37° C., and then was inoculated in a bioreactor containing the LPJ+50% OJ culture medium. Moreover, PB containing 0.15 g/L to 5 g/L of ammonium chloride was used as the control group, in which the carbon source was added with an equivalent amount to the carbon source of the experimental group LPJ+50% OJ. Thereafter, 10 g/L of sodium bicarbonate was added under the culture conditions of 34° C. and pH 7.2. Then, after anaerobic culture for 72 hours, the content of succinic acid was analyzed, and the results are shown in Table 14.

TABLE 14

Production of succinic acid by bacteria strain JD654
expressed in LPJ + 50% OJ culture medium

| Culture medium | Succinic acid (g/L) |
| --- | --- |
| LPJ + 50% OJ | 5.67 |
| PB | 1.17 |

Production of Lactic Acid by Fermentation

Experiment 8: Production of Lactic Acid with Pineapple Juice Produced by Different Processing Methods as Culture Medium 1. Origin and Pretreatment of Pineapple Juice Pineapple juice (PAJ) produced from pineapple waste refers to PAJ obtained by processing pineapple after removal of the usable pulp or overproduced pineapple waste containing peel, root, and leaf. The processing method thereof is the same as the three processing methods of abovementioned (A), (B), and (C) used in production of succinic acid, and is therefore not repeated herein.

2. Production of Lactic Acid Using Genetic Engineered Bacteria with (A) PAJ as Culture Medium A PAJ-based culture medium was provided, which contains PAJ (20 g/L to 40 g/L of glucose, 4 g/L to 34 g/L of sucrose, and 28 g/L to 53 g/L of fructose), PB solution, and 0.5 mM of IPTG. The bacteria strain PCI 627 was first cultured in LB culture medium overnight at 37° C., and then was inoculated in a bioreactor containing the (A) PAJ culture medium. Moreover, a PB containing 0.15 g/L to 5 g/L of ammonium chloride, 2.5 g/L of yeast extract, and 5 g/L of yeast extract were respectively used as control groups, in which the carbon source (glucose, sucrose, and fructose) was respectively added to each control group with an equivalent amount to the carbon source of the experimental group (A) PAJ. Thereafter, the control groups were aerobically cultured in a shake flask at 37° C. and pH 7 for 48 hours. Then the concentration of lactic acid was analyzed and the results are shown in Table 15.

TABLE 15

Production of lactic acid by bacteria strain PCI 627 expressed in groups of different culture media but same carbon source

| Culture medium | Produced lactic acid (g/L) |
| --- | --- |
| (A) PAJ | 7.51 |
| PB | 0.48 |
| 2.5 g/L yeast extract | 0.30 |
| 5 g/L yeast extract | 0.64 |

It can be known from the embodiments that, the genetic engineered bacteria of the embodiments of the disclosure can adopt a fruit and vegetable by-product or fruit and vegetable waste as the metabolic substrate to produce succinic acid or lactic acid. As a result, not only the fruit and vegetable by-products or vegetable waste can be effectively recycled, but also the production cost of succinic acid or lactic acid is significantly reduced, and the yield of succinic acid or lactic acid is increased.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A genetic engineered bacteria producing succinic acid by using a fruit and vegetable by-product or fruit and vegetable waste as a metabolic substrate, comprising:
  knock out genes related to producing succinic acid, wherein said knock out genes related to producing succinic acid consist of:
    a knock out endogenous ptsG gene;
    a knock out endogenous ldhA gene, wherein the knock out endogenous ldhA gene does not express lactate dehydrogenase (LDH);
    a knock out endogenous adhE gene, wherein the knock out endogenous adhE gene does not express alcohol dehydrogenase (ADH); and
    a knock out endogenous ackA-pta gene, wherein the knock out endogenous ackA-pta gene does not express acetate kinase and phosphotransacetylase (ACK-PTA);
  wherein the genetic engineered bacteria is cultured in a culture medium, and the culture medium comprises at least one fruit and vegetable by-product or fruit and vegetable waste as a carbon source of the genetic engineered bacteria to produce succinic acid, and wherein a total nitrogen content of the culture medium ranges from about 470 mg/L to 1740 mg/L, and the genetic engineered bacteria uses glucose, sucrose, and fructose as the carbon source.

2. The genetic engineered bacteria of claim 1, wherein the carbon source comprises 5 g/L to 50 g/L of glucose, 0.5 g/L to 50 g/L of sucrose, and 2 g/L to 60 g/L of fructose.

3. The genetic engineered bacteria of claim 1, wherein the culture medium further comprises about 1 g/L to 50 g/L sodium bicarbonate.

4. The genetic engineered bacteria of claim 1, wherein the culture medium has a culture temperature of 26° C. to 40° C. and a pH value ranging from 6 to 8.

5. The genetic engineered bacteria of claim 1, wherein the genetic engineered bacteria is cultured in the culture medium in an anaerobic or aerobic state.

6. The genetic engineered bacteria of claim 5, wherein the genetic engineered bacteria is cultured in the anaerobic state for 12 hours to 120 hours.

7. The genetic engineered bacteria of claim 5, wherein the genetic engineered bacteria is cultured in the aerobic state for 12 hours to 48 hours.

8. The genetic engineered bacteria of claim 1, wherein the fruit and vegetable by-product or fruit and vegetable waste comprises a by-product or waste of a temperate fruit, a subtropical fruit, a tropical fruit, and a root vegetable.

9. A method for producing succinic acid, comprising the following steps:
  providing the genetic engineered bacteria of claim 1;
  providing a culture medium, wherein the culture medium comprises at least one fruit and vegetable by-product or fruit and vegetable waste as a carbon source of the genetic engineered bacteria, wherein a total nitrogen content of the culture medium ranges from about 470 mg/L to 1740 mg/L;
  culturing the genetic engineered bacteria in the culture medium at a culture temperature of 26° C. to 40° C. and a pH range of 6 to 8 to produce a culture solution, such that the genetic engineered bacteria produces succinic acid into the culture solution with the fruit and vegetable by-product or fruit and vegetable waste as a metabolic substrate thereof;
  collecting the culture solution comprising succinic acid; and
  isolating succinic acid from the culture solution comprising succinic acid.

10. A genetic engineered bacteria producing lactic acid by using a fruit and vegetable by-product or fruit and vegetable waste as a metabolic substrate, comprising:
  knock out genes related to producing lactic acid, wherein the knock out genes related to producing lactic acid consist of:
    a knock out endogenous adhE gene, wherein the knock out endogenous adhE gene does not express alcohol dehydrogenase (ADH); and
    a knock out endogenous ackA-pta gene, wherein the knock out endogenous ackA-pta gene does not express acetate kinase and phosphotransacetylase (ACK-PTA);
  wherein the genetic engineered bacteria is cultured in a culture medium, and the culture medium comprises at least one fruit and vegetable by-product or fruit and vegetable waste as a carbon source of the genetic engineered bacteria to produce lactic acid, and wherein a total nitrogen content of the culture medium ranges from about 470 mg/L to 1740 mg/L, and the genetic engineered bacteria uses glucose, sucrose, and fructose as the carbon source.

11. The genetic engineered bacteria of claim 10, wherein the carbon source comprises 5 g/L to 50 g/L of glucose, 0.5 g/L to 50 g/L of sucrose, and 2 g/L to 60 g/L of fructose.

12. The genetic engineered bacteria of claim 10, wherein the culture medium further comprises about 1 g/L to 50 g/L sodium bicarbonate.

13. The genetic engineered bacteria of claim 10, wherein the culture medium has a culture temperature of 26° C. to 40° C. and a pH value ranging from 6 to 8.

14. The genetic engineered bacteria of claim 10, wherein the bacteria is cultured in the culture medium in an anaerobic or aerobic state.

15. The genetic engineered bacteria of claim 14, wherein the bacteria is cultured in the anaerobic state for 12 hours to 120 hours.

16. The genetic engineered bacteria of claim 14, wherein the bacteria is cultured in the aerobic state for 12 hours to 48 hours.

17. The genetic engineered bacteria of claim 10, wherein the fruit and vegetable by-product or fruit and vegetable waste comprises a by-product or waste of a temperate fruit, a subtropical fruit, a tropical fruit, and a root vegetable.

18. A method for producing lactic acid, comprising the following steps:
  providing the genetic engineered bacteria of claim 10;
  providing a culture medium, wherein the culture medium comprises at least one fruit and vegetable by-product or fruit and vegetable waste as a carbon source of the genetic engineered bacteria, wherein a total nitrogen content of the culture medium ranges from about 470 mg/L to 1740 mg/L;
  culturing the genetic engineered bacteria in the culture medium at a culture temperature of 26° C. to 40° C. and a pH range of 6 to 8 to produce a culture solution, such that the genetic engineered bacteria produces lactic acid into the culture solution with the fruit and vegetable by-product or fruit and vegetable waste as a metabolic substrate thereof;
  collecting the culture solution comprising lactic acid; and
  isolating lactic acid from the culture solution comprising lactic acid.

19. The method of claim 10, further comprising adding ammonium chloride into the culture medium in a range of 0.15 g/L to 5 g/L.

20. The method of claim 18, further comprising adding ammonium chloride into the culture medium in a range of 0.15 g/L to 5 g/L.

* * * * *